United States Patent [19]

Farina et al.

[11] Patent Number: 5,011,774

[45] Date of Patent: Apr. 30, 1991

[54] DIDEOXYINOSINE BY ENZYMATIC DEAMINATION OF DIDEOXYADENOSINE

[75] Inventors: Vittorio Farina, West Hartford, Conn.; Daniel A. Benigni, Elbridge; Paul R. Brodfuehrer, Syracuse, both of N.Y.

[73] Assignee: Bristol-Myers Squibb Co., New York, N.Y.

[21] Appl. No.: 486,701

[22] Filed: Feb. 28, 1990

Related U.S. Application Data

[63] Continuation-in-part of Ser. No. 74,844, Jul. 17, 1987.

[51] Int. Cl.$^5$ .................... C12P 19/38; C12P 19/40; C12N 9/96; C12N 9/78
[52] U.S. Cl. .......................... 435/87; 435/88; 435/183; 435/188; 435/227; 435/280
[58] Field of Search ............... 435/87, 88, 183, 188, 435/227, 280

[56] References Cited

FOREIGN PATENT DOCUMENTS

1058209  5/1959  Fed. Rep. of Germany ........ 435/87
0004511  2/1972  Japan ................................... 435/89

OTHER PUBLICATIONS

Rosemeyer et al., Eur. J. Biochem. 122:375–380 (1982).
Prisbe et al., *Synth. Communications*, 15, 401 (1985) (1/11).
Webb et al., *Nucleosides and Nucleotides*, 7, (2), 147–143 (1988).

Primary Examiner—Robert A. Wax
Assistant Examiner—Stephanie W. Zitomer
Attorney, Agent, or Firm—Richard P. Ryan

[57] ABSTRACT

A novel process utilizing adenosine deaminase to selectively produce $\beta$-(D)-2',3'-dideoxyinosine in high yields from an $\alpha,\beta$-anomeric mixture. $\beta$-(D)-2',3'-Dideoxyinosine so produced is useful as an antiviral and antibiotic agent.

3 Claims, No Drawings

DIDEOXYINOSINE BY ENZYMATIC DEAMINATION OF DIDEOXYADENOSINE

CROSS REFERENCE

This is a continuation-in-part of U.S. Ser. No. 07/074,844 filed July 17, 1987.

BACKGROUND OF THE INVENTION

1. Field of the Invention

This invention relates to an improved process to produce β-(d)2′,3-dideoxyinosine.

2. Background — Related References

Typically, 2′, 3′-dideoxycytidine (ddC) is synthesized from 2′-deoxycytidine[1,2]. This is a general method for the synthesis of 2,3′-dideoxynucleosides. The starting materials for this synthesis are, however, extremely expensive and not available in bulk. The reagents required for this deoxygenation, furthermore, are also quite costly.

U.S. Ser. No. 028,817 filed 20 Mar. 1987, owned in common by the assignee of this invention, discloses a process for producing 2′, 3′-dideoxynucleosides represented by the formula

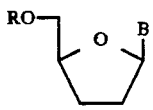

wherein B is a purine or pyrimidine base and R is H or a hydroxy-protecting group by the steps of (a) converting a γ-carboxy-γ-butyrolactone to a 5-0-hydroxy-protecting group-methyl-γ-butyrolactone, (b) converting the intermediate from step (a) to the 5-0-hydroxy-protecting group-methyl-2′,3′-dideoxypentofuranose, (c) converting the intermediate from step (b) to the 1-0-activating group -5-0-hydroxy-protecting group methyl-2′, 3′-dideoxypentofuranose, (d) converting the intermediate from step (c) to the 1-leaving group-5-0-hydroxy-protecting group-2′, 3′-dideoxypentofuranose, (e) reacting the intermediate from step (d) with an activated purine or pyrimidine base, and (f) recovering the dideoxynucleoside from step (e). The resulting product comprises a mixture of β-and α-anomers which may be separated using chromatographic and crystallization techniques well-known in the field to which this invention relates.

There remains in the field a need for process improvements whereby the generally active, or more active, β-anomer of (D)-2′, 3′-dideoxynucleosides can be selectively obtained without the costly and time-consuming chromatographic or fractional recrystallization separation of β- and α-anomers. This is particularly important when large quantities of the desired β-anomeric form is desired.

Inosine, chemically 9-β-(D)-ribofuranosylhypoxanthine, biochemically results from enzymatic deamination of adenosine, chemically 9-β-(D)-ribofuranosyl-9H-purin-6-amino. This process, employing adenosine deaminase, acts to metabolically degrade purines to hypoxanthines for excretion in the higher animals. Inosine can be prepared from adenosine by incubation with purified adenosine deaminase obtained from biological sources, e.g. bovine intestine. In applications such as these, where natural substrates are involved, it is known that the enzyme selectively deaminates only one enantiomer of the racemic pair. Enzymatic specificity would not be known beforehand when anomeric mixtures of structurally modified nucleosides were presented as substrates. Specificity on the basis of the known enantiomeric selection process of the enzyme, is not the basis for specificity when applied to an anomeric mixture.

SUMMARY OF THE INVENTION

In summary, this invention comprises an efficient process for selectively producing β-(D)-2′, 3′-dideoxyinosine represented by the formula

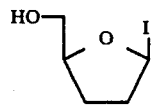

Formula A wherein I is the purine base, inosine. The process involves producing an α-,β-anomeric mixture of (D)-2′, 3′-dideoxyadenosine, which is then subjected to selective enzymatic deamination converting the adenosine base to inosine for only the β-(D)-isomer which is readily isolable and easily purified by simple recrystallization.

DETAILED DESCRIPTION OF THE INVENTION

The present invention is an improved process for selectively producing β-(D)-2′-3′-dideoxyinosine represented by the formula

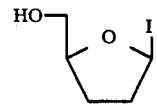

Formula A wherein I is the purine base, inosine which comprises the steps of:

1. preparing an anomeric mixture of α-and β-(D)-2′, 3′-dideoxyadenosine;
2. selectively deaminating the β-(D)-2′, 3′-dideoxyadenosine anomer by contact of the anomeric mixture of step 1. with the enzyme, adenosine deaminase; and
3. recovering the β-(D)-2′, 3′-dideoxyinosine produced in step 2.

A typical process for producing the anomeric mixture used in step 1. comprises the steps of:

(a) converting (D)- γ-carboxy-γ-butyrolactone of the formula

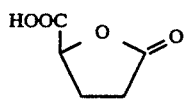

Formula 1 to a 5-0-hydroxy-protecting group-methyl-γ-butyrolactone of the formula

Formula 2 wherein R is a hydroxy-protecting group by reacting the Formula 1 compound with a carboxy group reducing agent followed by protecting the resulting hydroxymethyl group;

(b) converting the intermediate from step (a), Formula 2, to the 5-0-hydroxy-protecting group-methyl-2,3-dideoxy-(D)- pentofuranose of the formula

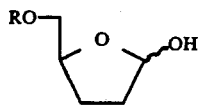

Formula 3 wherein R is a hydroxy-protecting group by reacting the Formula 2 compound with a carbonyl group reducing agent;

(c) converting the intermediate from step (b), Formula 3, to the 1-0-activating-group-5-0-hydroxy-protecting group-2,3-dideoxy-(D)- pentofuranose of the formula

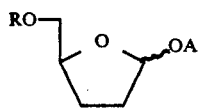

Formula 4 wherein R is a hydroxy-protecting group and A is an 0-activating group selected from alkylcarbonyl, arylcarbonyl, alkylthiocarbonyl, arylthiocarbonyl, alkylsulfonyl, arylsulfonyl and carbonate groups, wherein the alkyl moiety may be an unsubstituted or substituted $C_1$-$C_3$ alkyl group and the aryl moiety may be an unsubstituted or substituted phenyl group and wherein the substituent on the alkyl and aryl moieties may be selected from 1 to 3 groups selected from halo and $C_1$-$C_3$ alkoxy groups by reacting the Formula 4 compound with an acylating or sulfonating or carbonylating agents corresponding to group A above;

(d) converting the intermediate from step (c), Formula 4, by reaction with a compound having one of the formulas HX and trimethylsilyl halide to the 1-leaving-group-5-0-protecting group-2,3-dideoxy-(D)- pentofuranose of the formula

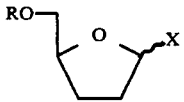

Formula 5 wherein R is a hydroxy-protecting group and X is a leaving group selected from F, Cl, Br and I;

(e) reacting the intermediate from step (d), Formula 5, with an activated derivative of adenine, wherein the base, adenine, has been activated by means of reacting the pendant amino and hydroxy groups on the adenine nucleus with an activating compound selected from silylating and acetylating and benzoylating agents, and optionally, in the presence of one of a Bronsted acid and a Lewis acid and in the presence of an inert organic solvent; and (f) recovering the anomeric mixture of α-and β-(D)-2'3'-dideoxyadenosine after cleavage of the 5-0-hydroxyprote group from the intermediate product of step (e) above.

The starting material, (D)-γcarboxy-γ-butyrolactone be conveniently obtained from L-glutamic acid by utilizing conventional techniques reported in the chemical literature[3].

A combination of chemical reactions produce a suitably blocked 2,3-dideoxypentofuranose, 3. This compound and its derivatives are known in the literature.

Thus, the conversion of the starting material, (D)-γ-carboxy-γ-butyrolactone, to a 5-0-hydroxy-protecting group-methyl-γ-butyrolactone, step (a), involves the reduction of the γ-carboxy group to a hydroxymethyl group followed by reaction with a hydroxy-protecting group reagent. For example, the reduction of the γ-carboxy group and protection of the resulting γ-hydroxymethyl group by means of the benzyl group ($PhCH_2$—), step (a), was achieved by the successive reaction of the starting compound of Formula 1 with $BH_3.SMe_2$ and $PhCH_2Br$.

The primary alcohol functional group may be protected as an ether, such as trialkyl or dialkyl aryl or diaryl alkyl or triaryl silyl, unsubstituted and substituted benzyl, unsubstituted and substituted alkyl, or allyl ether, or as an ester, such as a benzoyl, mesitoyl, pivaloyl, unsubstituted or substituted acetyl, or a carbonate ester. See "Protective Groups in Organic Synthesis," T. W. Greene, John Wiley, N.Y. 1981 for more detailed description of protecting groups and the chemistry relating to the same. In a more preferred embodiment, there was used as the hydroxy-protecting group for the primary alcohol group at the 5-position the benzyl group, and most preferably the benzoyl group, because of their stability and well-known preparation.

The conversion of the 5-0-hydroxy-protecting group-γ-butyrolactone, to the 5-0-hydroxy-protecting group-2,3-dideoxypentofuranose having Formula 3 in step (b) was achieved by reacting the intermediate having Formula 2 with NaH and $HCO_2Et$ followed by HCl.

It will be understood by those skilled in the art to which this invention relates that any one of a number of reducing agents may be used to carry out either or both of steps (a) and (b) independently (i.e., in succession) or at the same time. Other useful reducing agents besides $BH_3.SMe_2$ used in steps (a) and (b) as described above include $NaBH_4$, $NaBH_4$ plus LiCl or $AlCl_3$ or $BF_3$, $LiAlH_4$, $LiAlH(OMe)_3$, $LiAlH(O-t-Bu)_3$, $(Sia)_2BH$ (disiamyl borane) and other dialkylboranes, and the like. Disiamyl borane is preferred as the reducing agent because of its convenient handling and reactivity.

The step (c) conversion of the intermediate having Formula 3 to the intermediate having Formula 4 bearing an "activated" hydroxy group at the C(1) position of the 2,3-dideoxypentofuranose ring system may be achieved by any reagent effective to convert this hydroxy group to a group which may be displaced readily by Cl or Br upon reaction with HCl or HBr or, preferably, TMSBr or TMSCl (+) catalytic amount of TMSI. ("TMS" represents the trimethylsilyl group). Such a group which can be so displaced readily include 0-activating groups selected from alkylcarbonyl, arylcarbonyl, alkylthiocarbonyl, arylthiocarbonyl, alkylsulfonyl, arylsulfonyl and carbonate groups wherein the alkyl moiety may be an unsubstituted or substituted $C_1$-$C_3$ alkyl group and the aryl moiety may be an unsubstituted or substituted phenyl group and wherein the substituent on the alkyl and aryl moieties may be selected from 1 to 3 groups selected from halo and $C_1$-$C_3$ alkoxy groups. More preferably, this activating group is selected from corresponding (to the above) acetoxy and benzoyloxy groups and, most preferably, acetoxy. Step (c) was conveniently carried-out using acetic anhydride/pyridine reagent.

The step (d) displacement of the 1-0-activating group functional group with a leaving group selected from Cl and Br was achieved by treatment of 4 with HCl (or HBr) in $CH_2Cl_2$ at low temperature to give the furanosyl halides 5a and 5b, which are present in solution as a mixture of anomers ($\alpha$ and $\beta$).

In step (e) of the process according to this invention, the intermediate having Formula 5 from step (d) above was reacted with adenine activated by reaction with well-known activating reagents to obtain a silylated, acetylated or benzoylated or other acylated adenine, in the presence of a suitable polar or non-polar solvent and, optionally, in the presence of a Lewis acid such as, for example, boron halides, aluminum halides, titanium halides, tin (IV) chloride, zinc halides, trimethylsilyl bromide, iodide, triflate and any other species well-known to be used in glycosylation reactions or in the presence of a Bronsted acid such as hydrogen chloride, bromide or iodide. Especially useful in this step (e) is the use of silylated adenine in the presence of non-polar solvents such as, for example, benzene, toluene, chloroform, dichloromethane, dichloroethane and carbon tetrachloride. Examples of useful polar solvents include others such as tetrahydrofuran and dioxane, nitriles such as acetonitrile, dimethylformamide, and dimethylsulfoxide. An example of a useful procedure to carry out step (e) is disclosed in Brundidge et al., U.S. Pat. No. 4,625,020 which discloses the coupling of silylated pyrimidines, wherein active hydrogens of hydroxy and amino groups are blocked by silyl groups such as the trimethylsilyl group, with a 2-deoxy-2-fluoroarabinofuranosyl halide. As this referenced procedure was applied to step (e) an adenine base having all active amino hydrogens blocked by the trimethylsilyl group was reacted with an intermediate having Formula 5.

Thus treatment of intermediate having Formula 5 with a silylated adenine as defined above in $CH_2Cl_2$ and $CHCl_3$ gave protected (D)-2',3-dideoxyadenosine as a mixture of anomers.

Alternatively, in a variation, when in step (c) the group "A" is acetyl, the intermediate from step (c) may be reacted with an activated adenine derivative in the presence of a Lewis acid as in step (e) so as to obtain the 5-0-hydroxy-protecting group -2', 3'-dideoxyadenosine product without proceeding through step (d).

As mentioned above, in still another, more preferred embodiment according to this invention, the 1-0-acetyl-5-0-benzoyl-2,3-pentofuranose of Formula 4 from step (c) was contacted first with bromotrimethylsilane followed by a bis-silyl adenine to obtain in a single step, without isolation of the 1-bromo-5-0-benzoyl-2,3-pentofuranose intermediate as from step (d), to obtain 5'-0-benzoyl-2',3'-dideoxyadenosine as the product from the combined steps (d) and (e).

In step (f) of the process according to the present invention, the 5'-0-benzoyl-2', 3'-dideoxyadenosine was subjected to chemical reaction to remove the 5-0-protecting group. Suitable procedures to remove this protecting group are well-known in the field to which this invention relates and examples are disclosed in "Protective Groups in Organic Synthesis" by T. W. Greene, John Wiley, N.Y. 1981 mentioned above. More preferably, 5'-0-benzoyl-2',3'-dideoxyadenosine was subjected to methanol saturated with ammonia to obtain 2', 3'-dideoxyadenosine as a mixture of $\alpha$-and $\beta$-anomers.

In step 2. of the claimed instant process according to this invention, the mixture of $\alpha$-and $\beta$-(D)-2', 3'-dideoxyadenosine from step 1. was contacted with the enzyme, adenosine deaminase (ADA), isolated from calf spleen, in a neutral aqueous medium. This enzyme selectively catalyzes the deamination of the $\beta$-anomer of (D)-2', 3'-dideoxyadenosine to yield quantitatively $\beta$-(D)-2',3'-dideoxyinosine. Although adenosine deaminase (ADA) from calf spleen was used in the actual examples, it is believed that any preparation of adenosine aminohydrolase ("deaminase," EC 3.5.4.4) would be suitable. Thus, the use of any preparation of adenosine aminohydrolase (or "deaminase") effective to selectively deaminate the $\beta$-2', 3'-dideoxyadenosine anomer is within the scope of the process claimed as the present invention. Accordingly, in addition to the use of the free enzyme in an appropriate medium, such as in a neutral aqueous medium described herein, there may be used the enzyme, ADA, immobilized on an appropriate compatible substrate such as, for example, the oxirane-acrylic polymer substrate Eupergit C TM (Rohm Pharma Gmb). The ADA may be bound to the polymer using conventional techniques.

The (D)-2', 3'-dideoxyinosine product, was conveniently recovered by collecting the reaction mixture from step 2., removing insoluble reactants and additives by filtration through Celite, and purifying the resulting product by simple recrystallization, methanol being a preferred recrystallization solvent. In step 2., a catalytic to approximately equimolar to an excess amount of adenosine deaminase is added to the anomeric mixture of (D)-2',3'-dideoxyadenosine from step 1. in a suitable solvent. While a variety of solvents may be used, polar solvents, e.g. water or alcohol, are preferred. The reaction is essentially complete after a period of time which can range from less than an hour to several hours, depending on amount of enzyme, reaction condition, and the like. The reaction is preferably conducted for about 1 to 4 hours at about 20°–25° C.

In order to suppress contaminating amounts of deaminated $\alpha$-anomer from appearing in the product, the progress of the reaction should be followed to determine the maximum contact time, according to procedure well-known to those skilled in the art, e.g. thin-layer chromatography or high pressure liquid chromatographic techniques.

As an indication of the unobviousness of this selective enzymatic deamination step, it was determined that in the (L)-anomeric mixture, it was the $\alpha$-anomer and not the $\beta$-anomer that is favored by rate of enzymatic deamination. Since adenosine deaminase tends to be a rather non-specific enzyme and quite reactive, evidenced by its action on modified substrates, it certainly would not be obvious beforehand that there would be an advantageous rate difference in deamination of the $\alpha$- and $\beta$-anomers of (D)-2', 3'-dideoxyadenosine.

The use of the enzyme, adenosine deaminase, according to the process of the present invention affords the advantage whereby the resulting anomers ($\beta$ and $\alpha$) need not be separated using costly and time-consuming chromatographic and crystallization techniques that heretofore have been well-known in the field to which this invention relates. The $\beta$-(D)-2', 3'-dideoxyinosine anomer is desired because it is the active anomer or is, at least, substantially more active as an antiviral agent than is the $\alpha$-anomer.

The process for producing $\beta$-(D)-2', 3'-dideoxyinosine according to this invention starting from the 5-0- hydroxy-protecting group-methyl-γ-butyrolactone, is outlined in Scheme I below.

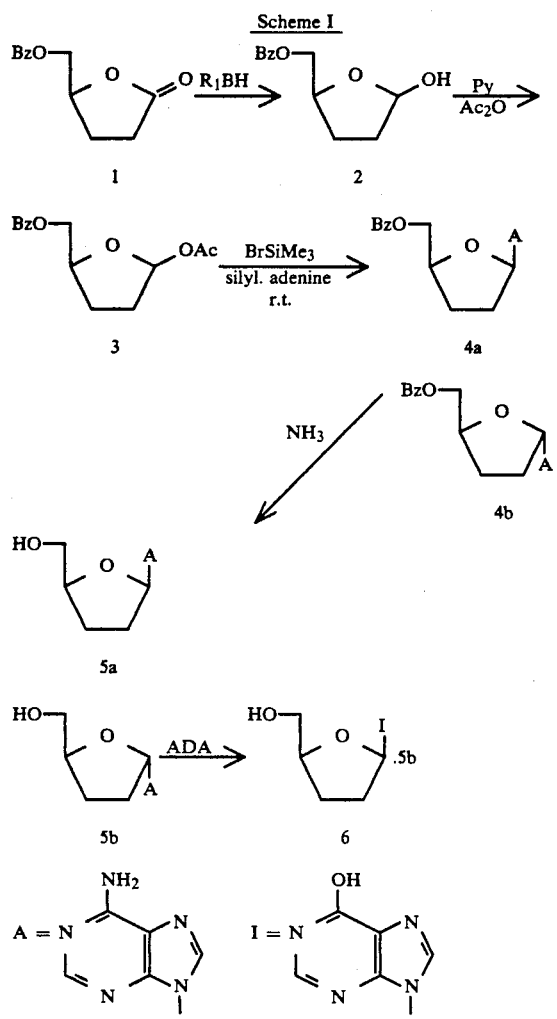

The following examples, wherein the compounds are numbered with reference to Scheme I, illustrate but a few representative embodiments of the process according to this invention and are not to be construed as limiting in scope. All parts and percentages are by weight and temperatures are in degrees Celsius unless otherwise specified.

EXPERIMENTAL

Example 1:

(D)-5-0-Benzyl-2,3-dideoxypentofuranose.(2) To 200 mL of a 0.5 M solution of disiamylborane in THF solution at 0° C. was added dropwise under nitrogen a solution of 15.1 g (0.069 mole) of (D)-5'-benzoyloxy-5-hydroxymethylbutyrolactone, 1, in 50 mL of dry tetrahydrofuran. After 20 min at 0° C. the reaction was warmed to 22° C. The reaction was stirred at 22° C. for 16 hrs, then worked up by slowly adding 12 mL of water and refluxing for 30 min. The reaction mixture was cooled to 0° C. followed by the slow addition of 24 mL of 30% hydrogen peroxide maintaining the pH between 7-8 with 1N sodium hydroxide. After the addition the reaction was evaporated under reduced pressure on a rotovapor at 30° C. to an oily residue. This was partitioned between 500 mL dichloromethane and 150 mL water. The aqueous layer was extracted with 2×100 mL dichloromethane and then the combined organic layers were washed with 50 mL water, dried over anhydrous sodium sulfate and evaporated to an oil. Yield=15.3 g (100%) of 5-0-benzoyl-2,3-dideoxypentofuranose. The $^1$H-NMR was consistent for structure and the oil was used directly in the next step.

Example 2

1-0-Acetyl-5-0-benzoyl-2,3-dideoxypentofuranose. (3)

A solution of 5-0-benzoyl-2,3-dideoxypentofuranose (15.3 g, 0.069 mole) in 32 mL of pyridine and 16 mL of acetic anhydride was stirred at 22° C. for 4 hrs then diluted with 500 mL dichloromethane and 100 g of ice was added. The reaction mixture was then washed with 3×100 mL 1N hydrochloric acid 3×100 mL saturated aqueous sodium bicarbonate and 100 mL of brine. The organic layer was dried over sodium sulfate and evaporated to yield a pale yellow oil. This could be used as is or chromatographed on silica gel 35%→60% EtOAc/hexane. Yield: 15.9 g (87%) of 1-0-acetyl-5-0-benzoyl-2,3-dideoxy-pentofuranose. Its NMR was consistent for structure.

Example 3

5'-0-benzoyl-2',3-dideoxyadenosine. (4)

1-0-acetyl-5-0-benzoyl-2,3-pentofuranose (0.522 g, 0.00198 mole) was dissolved in 5 mL of 1,2-dichloroethane. To this was added 276 μL (1.2 eq) of trimethylsilylbromide. This was stirred at 22° C. for 15 min prior to the addition of 11.9 mL of a 0.2 M solution of bissilyladenine in 1,2-dichloroethane. The solution was stirred for 88 hrs at 22° C. The reaction was then worked up by cooling to 0° C., followed by pouring into 40 mL of cold saturated aqueous sodium bicarbonate. The reaction mixture was partitioned between 200 mL dichloromethane and 2×40 mL cold saturated aqueous sodium bicarbonate and 40 mL brine. The organic layer was dried and evaporated to yield a colorless oil that was chromatographed on silica gel and eluted with 8% methanol in methylene chloride. Fractions were collected and similar ones pooled to yield 420 mg 5'-0-benzoyl-2',3'-dideoxyadenosine as a mixture of anomers (63%).

Example 4:

2', 3'-Dideoxyinosine. (6)

This mixture of anomers (1.66 g) was treated with 170 mL of methanol saturated with ammonia. This was tightly stoppered and stirred at 18° C. for 48 hrs. TLC indicated that reaction was incomplete. The solvent was evaporated and replaced with 170 mL of fresh ammonia solution in methanol. TLC after an additional 48 hr implied the reaction was complete. Hence, the solvent was evaporated and ethanol was added (5 mL). This yielded colorless crystals which were collected and washed with (5 mL) of 95% ethanol to yield 1.20 g (95%) of 2', 3'-dideoxyadenosine 5a together with its α anomer 5b in a 1:1 ratio by $^1$H-NMR. The α+β2',3'-dideoxyadenosine mixture was dissolved in 50 mL of deionized water and to this solution was added 10 mg of adenosine deaminase (type II, from Sigma; 9 units/mg→.9 μmole/min). The solution was stirred at 20° C. and reaction monitored by HPLC. After 2 hrs 30 min another 10 mg of adenosine deaminase was added. HPLC showed the reaction was nearly complete after 3 hrs. The reaction was then concentrated (1-2 mL) at 35° C. to give an oil. The oil was scratched and slowly diluted with 2×1.5 mL portions of methanol which produced white crystals. After 15 min the material was filtered and the colorless crystals washed with 2×1.5 mL portions of methanol to yield 2', 3'-dideoxyinosine (120 mg, 48%). The mother liquor was treated as above to yield an additional 29 mg (12%) of good quality product, which was characterized by $^1$H-NMR. The nuclear magnetic resonance spectrum was consistent with the structure.

REFERENCES

1. Samukov, V. V.; Ofitserov, V. I. Bioorg. Khim. 1983, 9, 132.
2. Prisbe, E. J.; Martin, J. C. synth. Commun. 1985, 15, 401.
3. Taniguchi, M.; Koga, K.; Yamada, S. Tetrahedron 1974, 30. 3547.

We claim:

1. An improved method for selectively producing β-(D)-2',3'-dideoxyinosine which comprises treatment of an α-and β-anomeric mixture of (D)-2',3'-dideoxyadenosine with adenosine deaminase while monitoring conversion of the preferantially deaminated β-anomer to control reduction time and minimize α-anomer deamination thereby maximizing production of β-(D)-2'-3'-dideoxyinosine which is recovered from the enzymatic reaction mixture.

2. The method of claim 1 wherein the adenosine deaminase is dissolved in a neutral aqueous medium for contact with the (D)-2',3'-dideoxyadenosine anomeric mixture.

3. The method of claim 1 wherein an immobilized adenosine deaminase preparation is utilized in the deamination process.

* * * * *